(12) United States Patent
Majlessi (10) Patent No.: US 7,632,289 B2
(45) Date of Patent: *Dec. 15, 2009

(54) HARVESTER

(76) Inventor: Heshmat Majlessi, 20 Stratford Rd., Harrison, NY (US) 10528

( * ) Notice: Subject to any disclaimer, the term of this patent is extended or adjusted under 35 U.S.C. 154(b) by 438 days.

This patent is subject to a terminal disclaimer.

(21) Appl. No.: 11/262,397

(22) Filed: Oct. 31, 2005

(65) Prior Publication Data

US 2007/0100359 A1    May 3, 2007

(51) Int. Cl.
*A61B 17/22* (2006.01)
(52) U.S. Cl. ....................... 606/159; 606/167
(58) Field of Classification Search ................ 606/159, 606/192, 171, 120, 169, 139, 222, 147, 153, 606/47, 1, 50; 600/473, 435, 564, 573; 604/22, 604/512
See application file for complete search history.

(56) References Cited

U.S. PATENT DOCUMENTS

| | | | | |
|---|---|---|---|---|
| 2,904,045 A | * | 9/1959 | Owings | ....................... 604/274 |
| 4,612,921 A | * | 9/1986 | Lazo de Zbikowski | ........ 606/57 |
| 5,364,395 A | * | 11/1994 | West, Jr. | ....................... 606/46 |
| 6,193,653 B1 | * | 2/2001 | Evans et al. | .................. 600/210 |
| 6,616,661 B2 | * | 9/2003 | Wellman et al. | ............... 606/50 |
| 2003/0130654 A1 | * | 7/2003 | Kasahara et al. | ............... 606/45 |
| 2003/0212389 A1 | * | 11/2003 | Durgin et al. | .................. 606/21 |
| 2004/0215226 A1 | * | 10/2004 | Majlessi | ..................... 606/190 |

* cited by examiner

*Primary Examiner*—Anhtuan T Nguyen
*Assistant Examiner*—Julie A Szpira
(74) *Attorney, Agent, or Firm*—Howard C. Miskin; Gloria Tsui-Yip (57) ABSTRACT

A device for removing and harvesting veins that minimizes the invasive nature of the procedure by providing an internal cutting device with an inner blade to sever the vein at the desired location from below the skin surface, after separation of the vein from the surrounding tissue. The device also includes a serrated cutting tip, a cutting system having a looped wire or two or more wires connected at the distal end of the device, which can be tightened to sever the vein in lieu of the use of the inner blade, or heated by a power source to cauterize the vein. An injection port and cannula may also be contained in the device for delivery of local anesthesia around the vein.

5 Claims, 8 Drawing Sheets

HARVESTER

CROSS REFERENCE TO RELATED APPLICATIONS

Not applicable

STATEMENT REGARDING FEDERALLY SPONSORED RESEARCH OR DEVELOPMENT

Not applicable

REFERENCE TO SEQUENCE LISTING, A TABLE, OR A COMPUTER PROGRAM LISTING COMPACT DISC APPENDIX

Not applicable

BACKGROUND OF THE INVENTION

The field of medical devices has numerous instruments fashioned to remove veins. Most of the procedures pertaining to the use of the known instruments require full anesthesia, and must be performed in a hospital, where the patient may experience pain, complications, and resulting scarring from the procedure.

The original Harvester, as disclosed by the applicant in patent application publication no. 20040215226, is hereby incorporated by reference. The original Harvester is an instrument used to harvest veins, and comprises a handle, an elongated shaft and a tip, which contains a blade. This instrument is used by rotating the tip around the vein designated to be removed, resulting in the separation of the outside wall of the vein from the surrounding tissue, without any damage to the vein itself. Although the method of use of the Harvester is notably less intrusive than the other available methods and uses of other instrumentation, it nonetheless results in an incision on the skin at the knee, because the distal end of the vein would be severed by means of a percutaneous blade.

The present invention is an improvement of the Harvester, because it embodies an internal blade system, eliminating the need for use of a percutaneous blade. It also provides a number of other additional components, such as a new serrated tip facilitating severance of the side branches of the vein, an injection port with a cannula, which can be inserted through the hollow shaft of the device, with the cannula having an ability to retract automatically following injection. Another additional component is a cauterization device comprising of two or more wires extending longitudinally through the hollow shaft of the surgical device, with a the distal end of each said wire connected to the distal end of the other said wire or wires, allowing the user to heat and sever the vein. These improvements result in a less invasive, and more efficient procedure.

BRIEF SUMMARY OF THE INVENTION

The disclosed invention is an improvement of a surgical instrument, used for removal of unwanted varicose veins or healthy veins of arms and legs for bypasses or fistula formulation. The original Harvester surgical instrument is a specialized device used by insertion of the instrument through the skin, by using a cutting edge located at the tip, and harvesting the desired length of the vein, completing the process by severing the vein by the use of a percutaneous blade. The Improved Harvester minimizes the invasive nature of the procedure, by embodying an internal cutting device within the instrument, to sever the vein at the desired location from below the skin surface, generally at the knee level, after separation of the vein from the surrounding tissue. The Improved Harvester also embodies other improvements. A new serrated cutting tip provides a greater degree of ease in separating the surrounding tissue from the vein to be harvested. Another improvement is the inclusion of a cauterization device, which can sever the vein in lieu of the use of the inner blade. The Improved Harvester also provides an injection port for delivery of local anesthesia to the tissue around the vein.

DESCRIPTION OF THE PREFERRED EMBODIMENTS

The Improved Harvester is an improvement of the vein removal surgical instrument, based on its embodiment of additional components, thereby allowing a less intrusive procedure and providing new means for separation of the vein from the surrounding tissue. It also provides a new injection port, used for injection of local anesthetic around the saphenous vein or any other veins.

Figure 4:
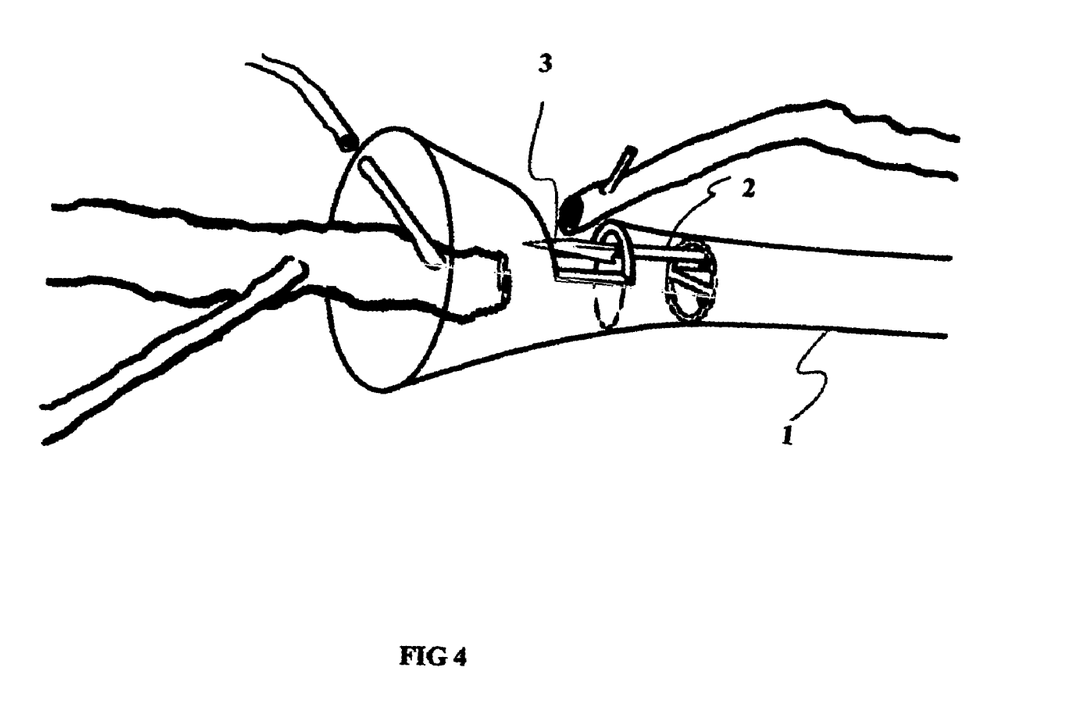
FIG. 4 is a perspective view of the cutting tip of the improved surgical instrument, showing the internal cutting device extended through the instrument, severing the vein.
Figure 6:
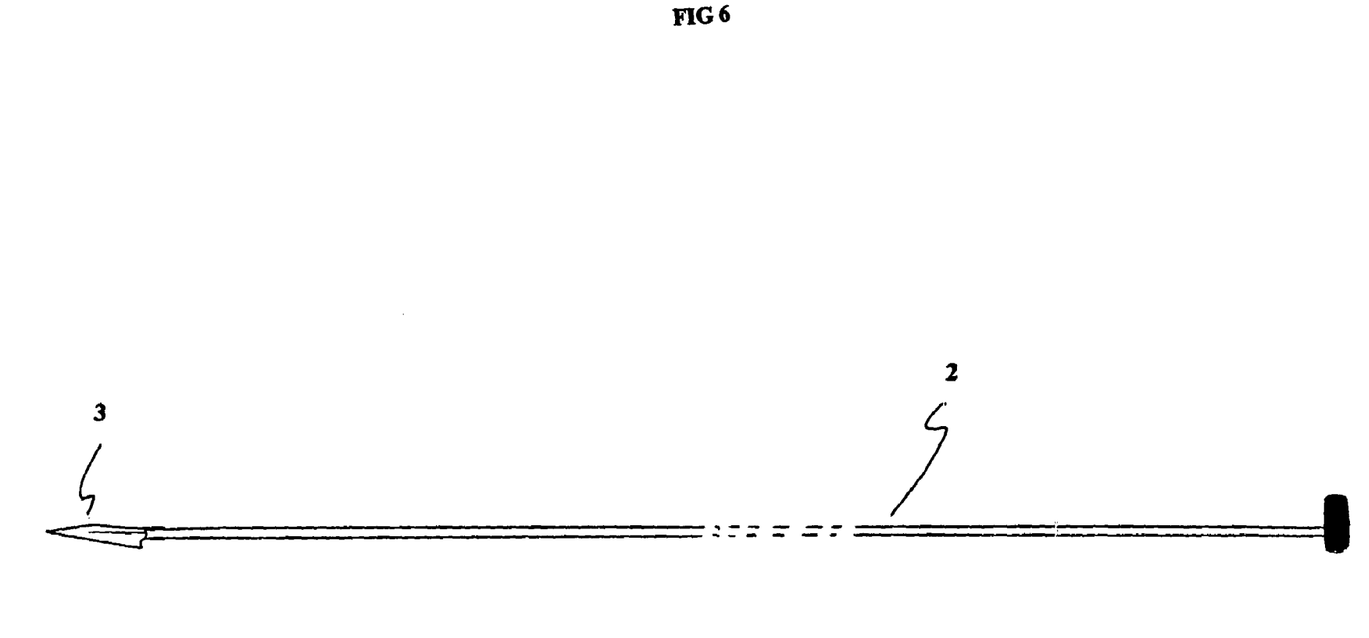
FIG. 6 is an elevational view of the inner cutting device used in one embodiment of the surgical device.
Figure 7:
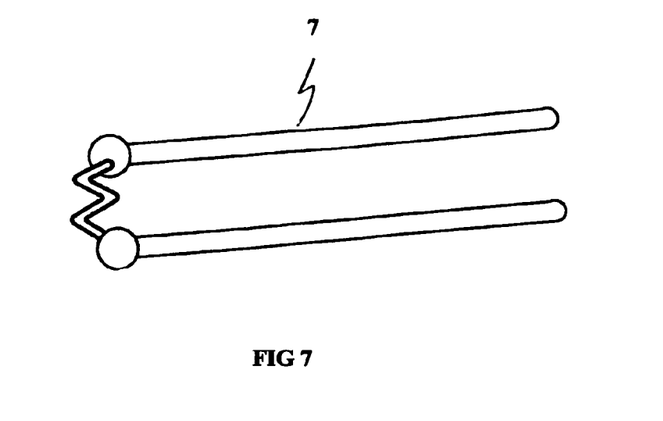
FIG. 7 is an elevational view of the distal end of the cautery device of one embodiment of the surgical device.
Figure 8:
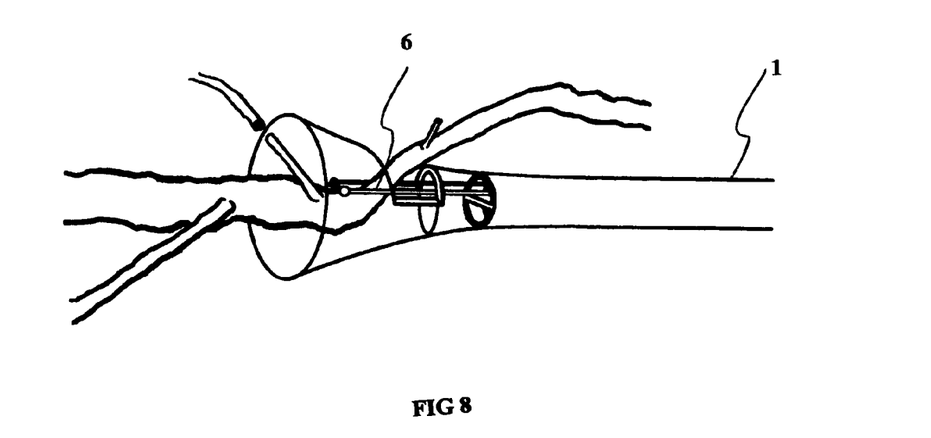
FIG. 8 is a perspective view of the cutting edge of the surgical device, showing the vein to be severed, in position for severance by use of the cautery device detailed in FIG. 7.
Figure 9:
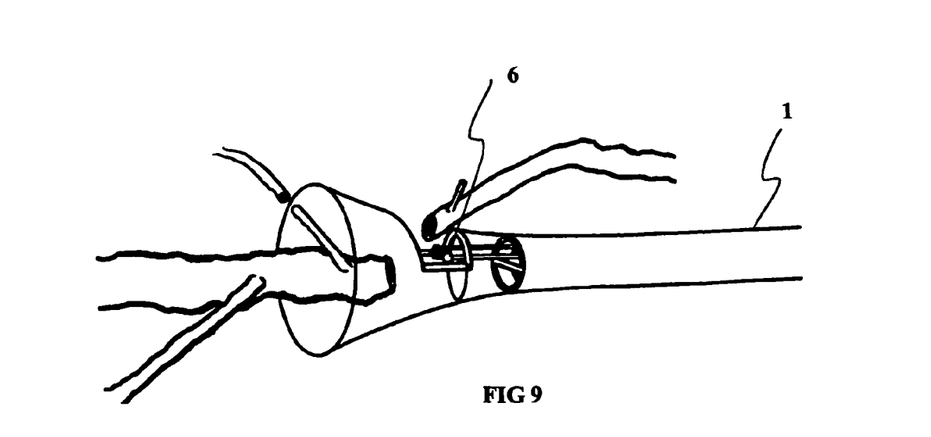
FIG. 9 is a perspective view of FIG. 8 but shows the surgical device and the vein subsequent to the severance of the vein by cauterization.

One of the new embodiments in the current invention is the inclusion of an inner cutting device 2 which is inserted through the hollow shaft 1 of the harvester, and contains a sharp cutting edge 3 at the distal end, allowing severance of the vein following the harvesting of the vein, thereby eliminating the need for an incision through the skin to sever the vein. The sharp cutting edge 3 can also be shaped in such manner to contain a pointed a tip 4, and sharp edges running along the length of the inner cutting device.

Figure 10:
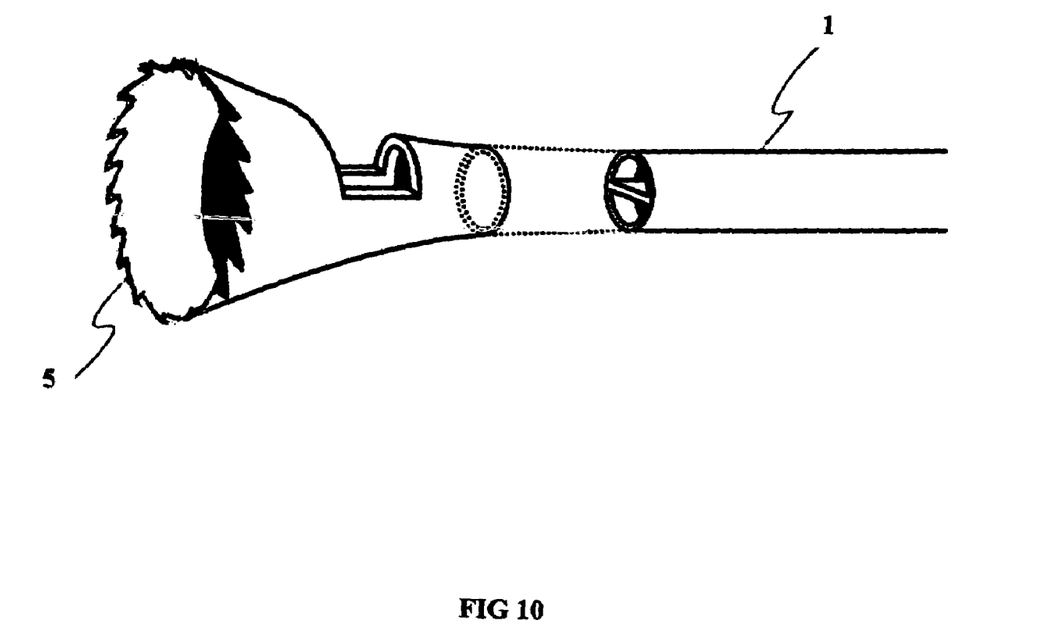
FIG. 10 is a perspective view of the cutting tip of one of the embodiments of the improved surgical instrument, showing the serrated edge of the cutting tip.

The improvement of the leading edge of the harvester is an enhanced cutting tip, which is serrated 5. The serration of the cutting edge assists in capturing and severing the side branches of the vein to be harvested. In general, a serrated tip 5 eases the advancement of the harvester for separation of the vein from the surrounding tissue, and improves the ability of the user to separate the surrounding tissue and excise the branching veins.

The Improved Harvester may also contain a device 6, comprised of two or more wires 7 constructed from any metal capable of being heated by a power source, said wires extending through the length of the hollow shaft of the harvester. This system allows the user to retract the wires 7 following placement of the connected end of the wires around the vein, and sever the vein. The said wires 7 may be connected to a power source 8, allowing the user to heat the wires 7, cauterizing the vein and improving the ability to sever the vein.

Figure 1:
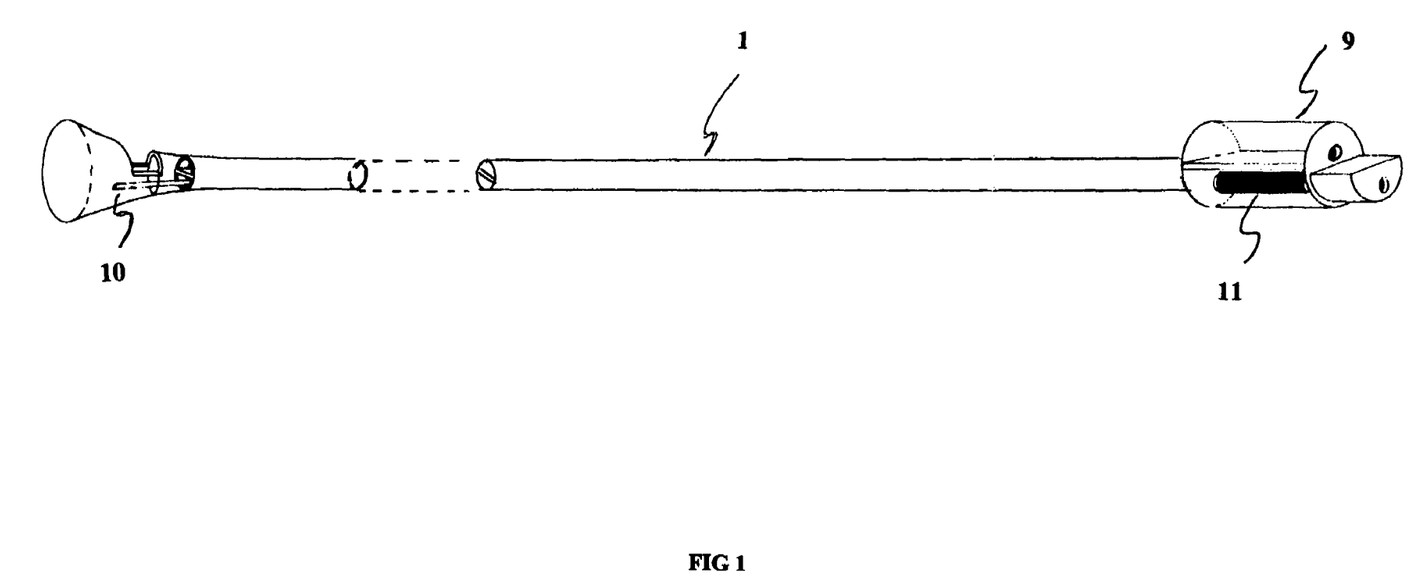
FIG. 1 is a perspective view of one embodiment of the improved surgical instrument with an injection port.
Figure 2:
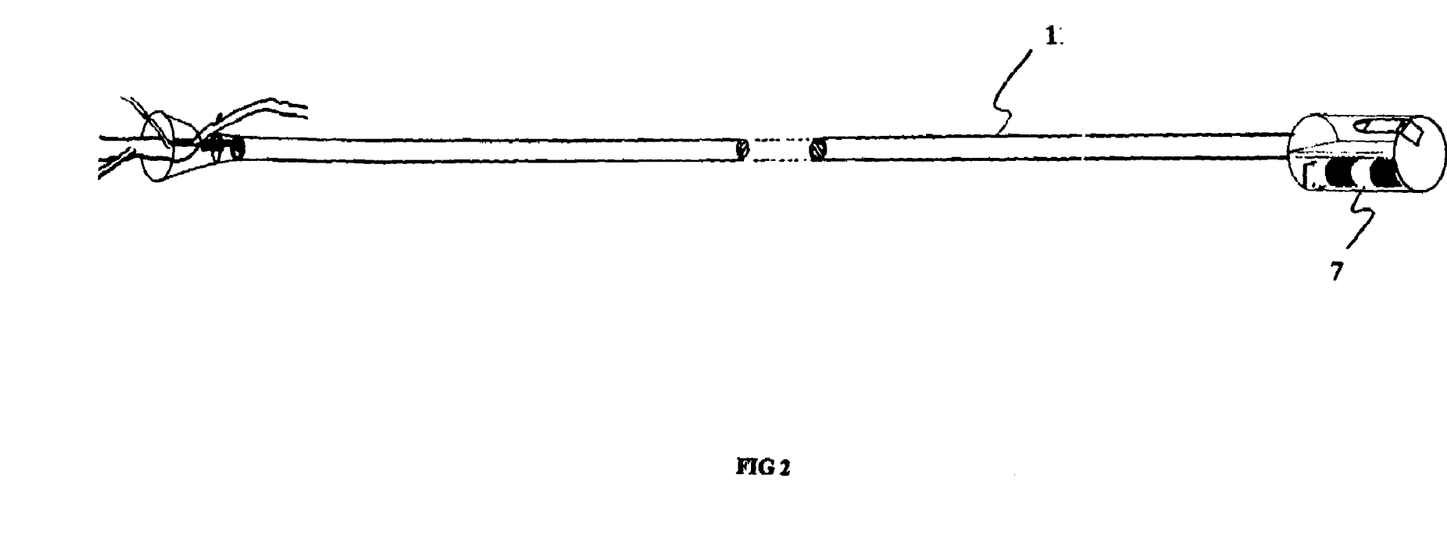
FIG. 2 is a perspective view of another embodiment of the improved surgical instrument with a cautery device powered by batteries contained within the proximal end of the said instrument.
Figure 3:
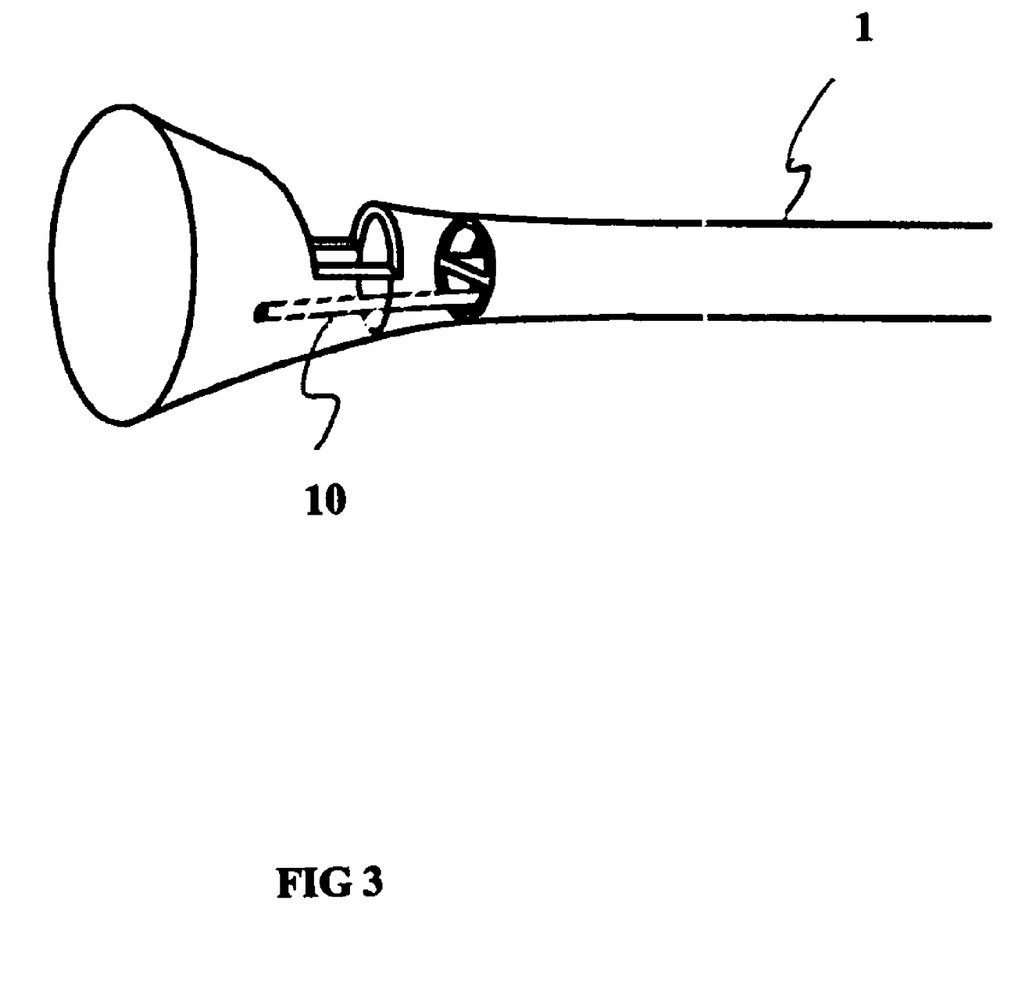
FIG. 3 is a perspective view of the cutting tip of one of the embodiments of the improved surgical instrument, showing the cannula within the hollow shaft of the instrument, with the cannula in the retracted position.
Figure 5:
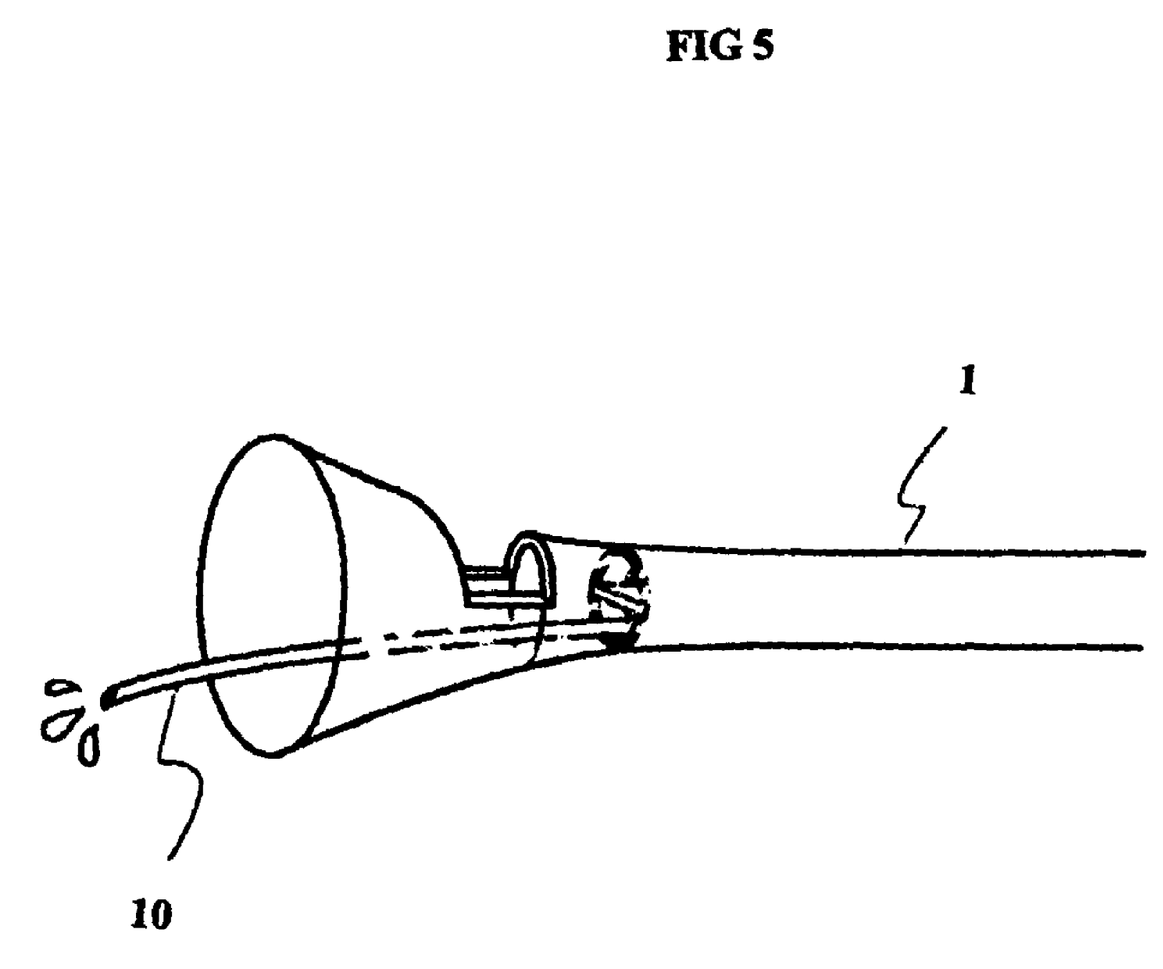
FIG. 5 is a perspective view of the cutting tip of one embodiment of the surgical device, showing the position of the cannula within the hollow shaft, with the cannula in the extended position.

There is also a new injection port 9, utilized for delivery of local anesthetic around the vein to be harvested. The injection port 9 is comprised of a cannula 10, located within the hollow shaft 1 of the harvester. The cannula 10 is used by advancing it though the harvester shaft 1, and thereafter administering the anesthetic to the tissue surrounding the vein. A variation of this injection port 9 allows for a means, such as a spring 11 located within the injection port 9, to spontaneously retract the cannula 10 into the harvester shaft 1, simplifying the use of the device.

The invention claimed is:

1. A surgical device for removing veins from the body of a patient comprising:
   a handle suitable for being gripped,
   a hollow, elongated shaft attached to said handle, having proximal and distal ends and defining an axis generally parallel to the length of said elongated shaft, a cutting tip in the form of an annular wall that tapers outwardly in a direction away from said axis located at said distal end, said cutting tip having a generally annular blade with a diameter greater than the diameter of a vein to be removed, said annular blade having serrations on said outwardly tapered annular wall to facilitate capture and severace of side branches of the vein and a cutting edge most remote from said handle generally facing a direction away from said handle for encircling and severing the vein to be removed from surrounding tissue by advancing the device with the vein received and passing through said annular blade, and
   an inner cutting device comprises a longitudinal member, having a proximal end and a distal end, and a length approximately comparable to that of said shaft, and a width which allows unhindered insertion through the interior hollow portion of said shaft, and a cutting blade located at said distal end of said longitudinal member, such that said cutting blade may be protruded from said distal end of said hollow shaft of said device, by longitudinal insertion of said cutting device through said shaft toward said distal end of said shaft wherein said cutting blade comprises a pointed tip and two or more sharp edges extending towards said proximal end of said inner cutting device.

2. A surgical device for removing veins from the body of a patient comprising:
   a handle suitable for being gripped,
   a hollow, elongated shaft attached to said handle, having proximal and distal ends and defining an axis generally parallel to the length of said elongated shaft, a cutting tip in the form of an annular wall that tapers outwardly in a direction away from said axis located at said distal end, said cutting tip having a generally annular blade with a diameter greater than the diameter of a vein to be removed, said annular blade having serrations on said outwardly tapered annular wall to facilitate capture and severace of side branches of the vein and a cutting edge most remote from said handle generally facing a direction away from said handle for encircling and severing the vein to be removed from surrounding tissue by advancing the device with the vein received and passing through said annular blade, and
   a vein severing device comprises one or more wires made of any malleable material, with said wire or wires extending longitudinally through said hollow shaft of said device, each of said wire forming a loop being retractable through said hollow shaft of said device.

3. The device as described in claim 2, wherein said vein severing device further comprises an electrical or power source located within said proximal end of said shaft, with said wires extending through said interior of said hollow shaft and connecting to said electrical or power source, said wires being capable of reaching a temperature sufficient for vein cauterization.

4. A surgical device for removing veins from the body of a patient comprising:
   a handle suitable for being gripped,
   a hollow, elongated shaft attached to said handle, having proximal and distal ends and defining an axis generally parallel to the length of said elongated shaft, a cutting tip in the form of an annular wall that tapers outwardly in a direction away from said axis located at said distal end, said cuffing tip having a generally annular blade with a diameter greater than the diameter of a vein to be removed, said annular blade having serrations on said outwardly tapered annular wall a cutting edge most remote from said handle generally facing a direction away from said handle for encircling and severing the vein to be removed from surrounding tissue by advancing the device with the vein received and passing through said annular blade, and
   an injection port comprises a cannula having a tip and a length longer than said hollow shaft of said device, said cannula being longitudinally located within the interior of said shaft, wherein said tip of said cannula can be extended through said distal end of said shaft by advancing the length of said cannula into said shaft.

5. The device as described in claim 4, further comprising a mechanical means located within said injection port for retracting said cannula into said hollow shaft of said device, allowing for spontaneous retraction of said cannula into said shaft in the longitudinal direction.

\* \* \* \* \*